US006312386B1

(12) United States Patent
Bolorforosh et al.

(10) Patent No.: US 6,312,386 B1
(45) Date of Patent: Nov. 6, 2001

(54) MEDICAL ULTRASOUND IMAGING SYSTEM WITH COMPOSITE DELAY PROFILE

(75) Inventors: Mirsaid Bolorforosh, Palo Alto; Ching-Hua Chou, Fremont; Albert Gee, Los Altos; Sungrung Huang, Los Gatos; Kutay Ustuner, Mountain View, all of CA (US)

(73) Assignee: Acuson Corporation, Mountain View, CA (US)

( * ) Notice: Subject to any disclaimer, the term of this patent is extended or adjusted under 35 U.S.C. 154(b) by 0 days.

(21) Appl. No.: 09/253,088

(22) Filed: Feb. 19, 1999

(51) Int. Cl.[7] ........................ A61B 8/00

(52) U.S. Cl. ........................ 600/447

(58) Field of Search ........................ 600/437, 440–441, 600/443, 447, 454–456; 73/625–626; 367/7, 11

(56) References Cited

U.S. PATENT DOCUMENTS

| | | | | |
|---|---|---|---|---|
| 4,813,279 | * | 3/1989 | Shirasaka | 73/626 |
| 5,111,824 | * | 5/1992 | Lazenby et al. | 600/447 |
| 5,113,706 | * | 5/1992 | Pittaro | 73/626 |
| 5,140,558 | * | 8/1992 | Harrison, Jr. et al. | 367/7 |
| 5,143,075 | * | 9/1992 | Ishizuka | 600/447 |
| 5,301,674 | * | 4/1994 | Erikson et al. | 600/447 |
| 5,402,792 | * | 4/1995 | Kimura | 600/471 |
| 5,579,770 | * | 12/1996 | Finger | 600/447 |
| 5,581,517 | * | 12/1996 | Gee et al. | 367/138 |
| 5,608,690 | | 3/1997 | Hossack et al. . | |
| 5,638,821 | * | 6/1997 | Nakamura et al. | 600/447 |
| 5,675,554 | | 10/1997 | Cole et al. . | |
| 5,696,737 | | 12/1997 | Hossack et al. . | |
| 5,740,128 | | 4/1998 | Hossack et al. . | |
| 5,951,479 | * | 9/1999 | Holm et al. | 600/447 |
| 6,056,693 | * | 5/2000 | Haider | 600/443 |

OTHER PUBLICATIONS

U.S. application No. 09/089,463.

* cited by examiner

*Primary Examiner*—Francis J. Jaworski
(74) *Attorney, Agent, or Firm*—Brinks Hofer Gilson & Lione

(57) ABSTRACT

A medical ultrasound diagnostic imaging system includes a delay system that applies a composite delay profile to signals to or from respective transducer elements. One composite delay profile includes a first, substantially point-focus delay profile for a first set of the transducer elements and a second, substantially point-focus delay profile for a second set of the transducer elements. The first and second delay profiles cause ultrasonic energy from the respective first and second sets of the transducer elements to constructively add at first and second respective spaced focal zones in either transmit or receive. Another composite delay profile includes first and second portions that substantially correspond to respective parts of a point-focus delay profile, and third and fourth portions that are intermediate the point-focus delay profile and respective tangents.

28 Claims, 8 Drawing Sheets

MEDICAL ULTRASOUND IMAGING SYSTEM WITH COMPOSITE DELAY PROFILE

BACKGROUND

This invention relates to medical ultrasound diagnostic imaging, and in particular to systems and methods for providing more effective focusing of ultrasound waveforms.

In current ultrasound imaging systems, transducer probes which include many individual transducer elements are operated as phased arrays.

Delay profiles are applied either to transmit waveforms or to receive waveforms associated with individual transducer elements in order to achieve desired focusing characteristics. One prior-art approach is to use a simple delay profile in which all of the transducer elements of the transducer probe are focused at a single focal point. Another prior-art approach is to use a delay profile that provides a distributed focus, as for example the well-known Axicon profile that provides a line focus.

A third prior-art approach is to transmit two or more transmit focal zones simultaneously. This is typically done by superimposing two separate delay profiles such that each transducer element generates ultrasonic energy that focuses at each of the two or more focal zones. This approach is known as the multi-focus approach, and is described in U.S. Pat. Nos. 5,696,737, 5,675,554, 5,608,690, 5,740,128, as well as in U.S. patent application Ser. No. 09/089,463.

The Axicon focus is typically associated with large side lobe levels that can represent a substantial disadvantage in many clinical applications. The simultaneous transmission of multiple focal zones generally requires dedicated beamformer hardware. Also, if the probe is limited by regulatory power or thermal limits, then the use of the multi-focus approach may require reduced power which in turn is generally associated with a reduction in the signal to noise ratio.

Another approach for increasing depth to field includes the use of multiple sequential transmit events focused at respective ranges along with the same ultrasound line. This approach reduces the frame rate, though it can substantially increase the depth of field.

Thus, a need presently exists for an improved approach that increases depth of field while avoiding some or all of the disadvantages discussed above.

BRIEF SUMMARY

The preferred embodiments described below use several different types of composite delay profiles that have the advantage of extending depth of field while maintaining a high frame rate and reducing side lobe problems.

Some of the embodiments described below use a composite delay profile having at least a first, substantially point-focus delay profile for a first set of the transducer elements and a second, substantially point-focus delay profile for a second set of the transducer elements. The first and second delay profiles cause ultrasonic energy from the respective first and second sets of the transducer elements to constructively add at first and second respective spaced focal zones. This composite delay profile can be used either in the transmitter or the receiver of an ultrasound imaging system.

Other embodiments described below use a delay profile that includes first and second portions corresponding to respective parts of a point-focus delay profile, a third portion intermediate the point-focus delay profile and a first tangent to the point-focus delay profile, and a fourth portion intermediate the point-focus delay profile and a second tangent to the point-focus delay profile.

The foregoing discussion of the preferred embodiments has been provided only by way of introduction, and nothing in the section should be taken as a limitation on the following claims.

DETAILED DESCRIPTION OF THE PRESENTLY PREFERRED EMBODIMENTS

Turning now to the drawings, FIGS. 1 through 5 illustrate components of ultrasonic imaging systems that can be used to implement the present invention, and FIGS. 6*b* through 13*b* provide information regarding composite delay profiles of selected embodiments of this invention.

Figure 1:
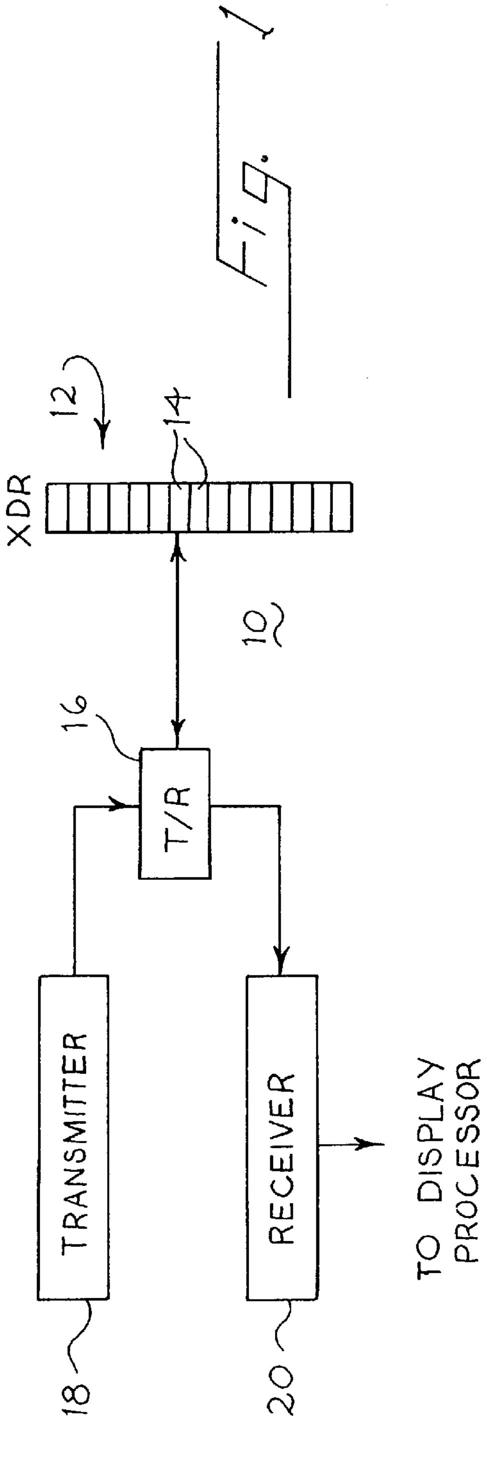
FIG. 1 is a block diagram of a medical diagnostic ultrasound imaging system.

As shown in FIG. 1, a medical diagnostic ultrasonic imaging system 10 includes a transducer probe 12 that in turn includes an array of individual transducer elements 14. The transducer probe 12 is connected by a transmit/receive switch 16 to a transmitter 18 and a receiver 20. The transmitter 18 applies respective transmit waveforms to the individual transducer elements 14 to cause the transducer probe 12 to form an ultrasonic transmit beam which is directed into an imaged region. Echoes from the imaged region impinge in the transducer elements 14, causing the transducer elements 14 to generate receive waveforms that are delayed and summed in the receiver 20 to form receive beams along desired receive lines. These receive beams are then applied to a display processor (not shown) for further processing and display.

Figure 2:
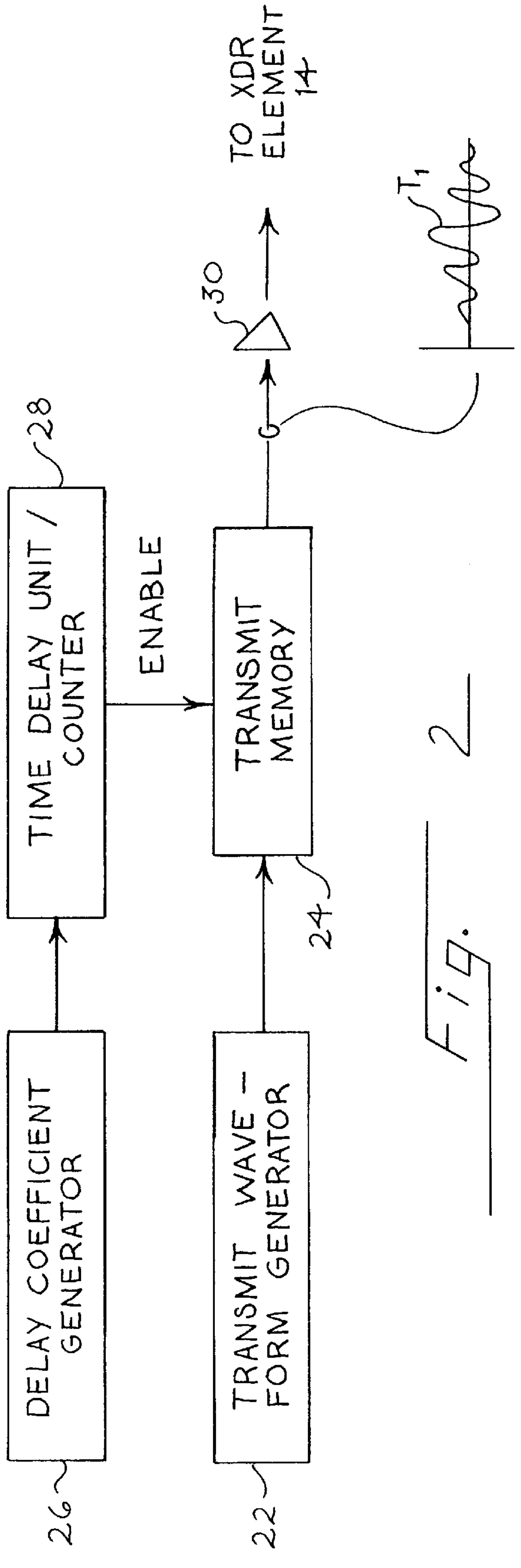
FIGS. 2 and 3 are block diagrams of portions of alternative embodiments of the transmitter of FIG. 1.
Figure 3:
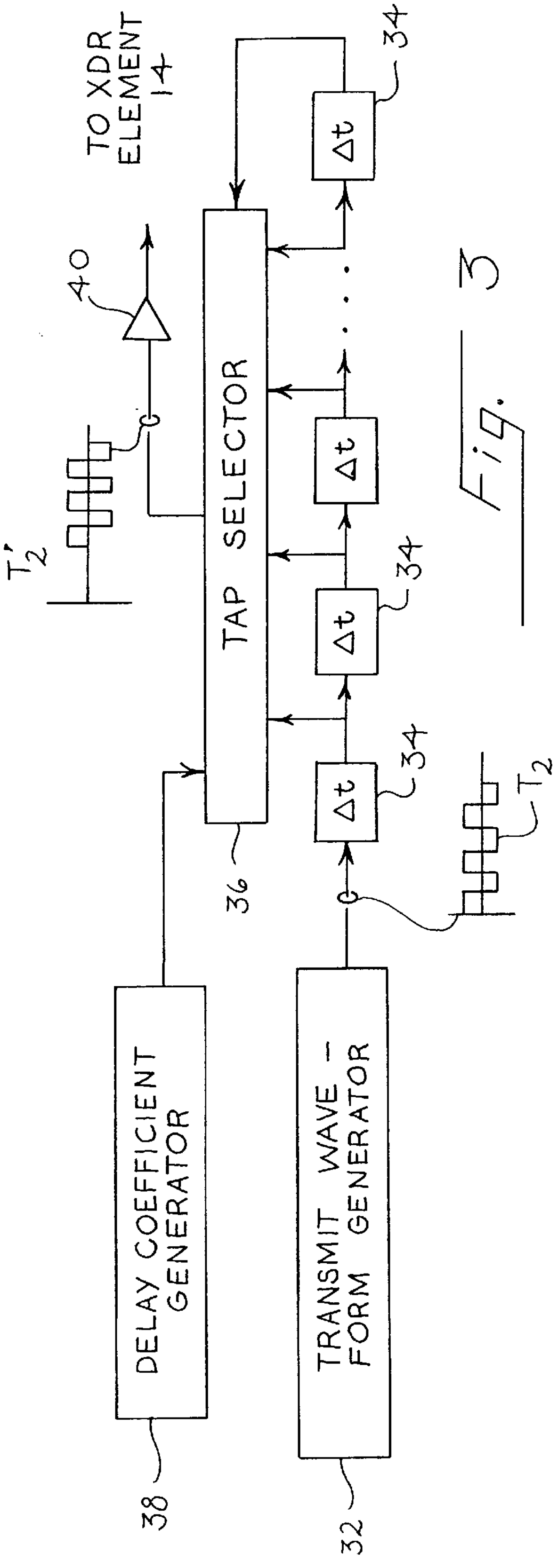
Figure 4:
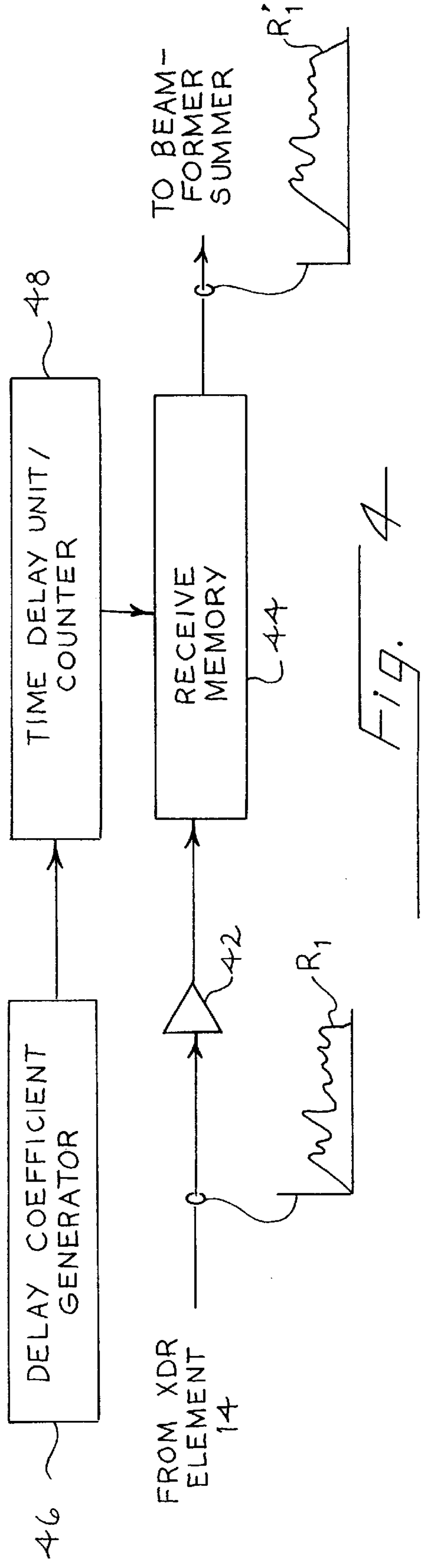
FIGS. 4 and 5 are block diagrams of portions of alternative embodiments of the receiver of FIG. 1.
Figure 5:
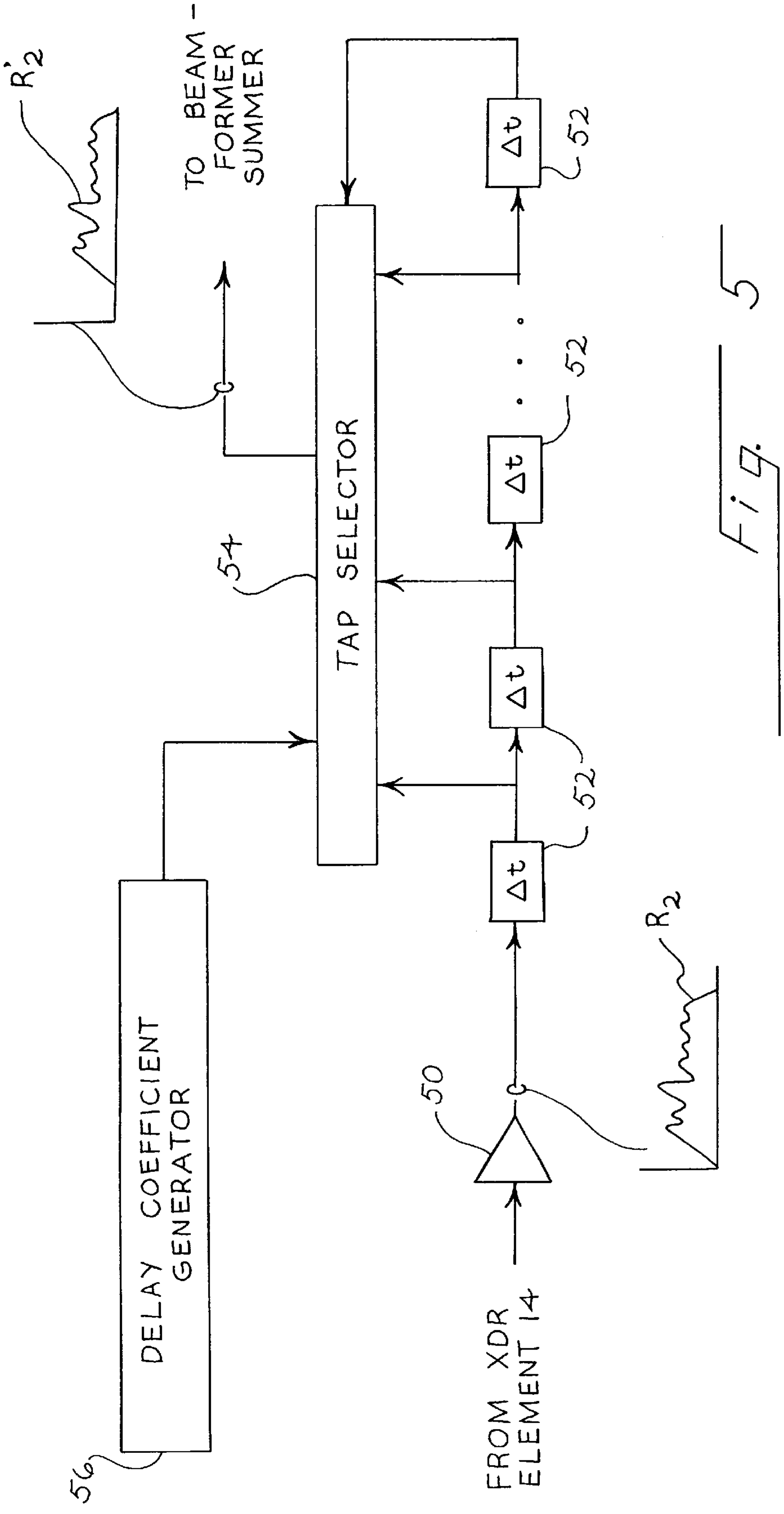

The present invention is useful in a wide variety of ultrasound imaging systems, and it is not intended to limit this invention to any particular hardware implementation. FIGS. 2 and 3 illustrate two alternative approaches for applying delays to transmit waveforms in the transmitter 18, and FIGS. 4 and 5 illustrate two alternative approaches to applying delays to receive waveforms in the receiver 20.

FIG. 2 shows a portion of a signal path for a delay system associated with a single transducer element 14 in the transmitter 18 of FIG. 1. In practice, the signal path of FIG. 2 would be replicated many times, with one replication for each group of one or more of the transducer elements 14. In the signal path of FIG. 2, a transmit waveform generator 22 generates a transmit waveform which is applied to a transmit memory 24. The transmit memory 24 is controlled by a time delay unit/counter 28 that is in turn controlled by a delay coefficient generator 26. The delay coefficient generator 26 calculates the time delay coefficient for the particular transducer element and loads this delay coefficient into the counter 28. Once the transmit waveform has been loaded into the transmit memory 24 and the counter 28 has been started to initiate a transmit event, the counter 28 counts down to zero, beginning at the stored delay coefficient, and then enables the transmit memory 24 to start transmission of the transmit waveform $T_1$ to a high voltage transmit amplifier 30 and then on to the associated transducer element 14. This is one example of how a digital transmitter can be used to apply a separate selected delay to the transmit waveform for each respective transducer element.

FIG. 3 shows another delay system suitable for use with analog transmitters. The signal path shown in FIG. 3 is suitable for a single transducer element, and would be replicated many times in a practical transmitter, once for each group of one or more transducer elements.

In the system of FIG. 3, a transmit waveform generator 32 applies a transmit waveform $T_2$ to a delay line that includes a number of sequential delay units 34. Each of the delay units 34 imposes a preselected time delay $\Delta t$ to the transmit waveform. The delayed transmit waveforms output by the respective delay units 34 are applied to a tap selector 36 that is controlled by a delay coefficient generator 38 such that one or more of the delayed transmit waveforms is applied by the tap selector 36 to a high voltage transmit amplifier 40, and then on to the respective transducer element.

The initial transmit waveform $T_2$ is shown in FIG. 3 as a bipolar rectangular pulse, and the time delayed transmit waveform $T_2'$ is shown as delayed with respect to the original transmit waveform $T_2$. In the system of FIG. 3, the delay coefficients are generated based on the desired delay profile, and the tap selector 36 activates the desired input based on the delay coefficient supplied by the delay coefficient generator 38. In many applications the output transmit waveform is amplified before being applied to the high voltage transmitter amplifier.

FIG. 4 shows a digital delay system suitable for use with a receiver such as the receiver 20 of FIG. 1. As before, FIG. 4 shows the signal path for only a single channel of the delay system, associated with a single group of one or more transducer elements. The receive waveform from the associated transducer element is amplified in an amplifier 42 and then loaded into a receive memory 44. The receive memory 44 is controlled by a time delay unit/counter 48 that operates in a manner similar to that of the counter 28 of FIG. 2. A delay coefficient generator 46 stores an appropriate delay coefficient in the counter 48, and when the counter 48 counts down from the stored delay coefficient to zero, the counter 48 enables the receive memory 44 to start transmission of the receive waveform to the beamformer summer that receives other receive waveforms from other signal paths similar to that of FIG. 4. In FIG. 4 the original, undelayed receive waveform $R_1$ is shown at the input to the receive memory 44, and the time delayed receive waveform $R_1'$ is shown at the output of the receive memory 44.

The delay system of FIG. 5 is an analog delay system that is similar to the analog delay system of FIG. 3. As shown in FIG. 5, the receive signal or waveform $R_2$ from a respective transducer element is amplified in the amplifier 50 and then applied to a delay line that includes multiple sequential delay units 52. The outputs of the respective delay units 52 are applied to a tap selector 54 that is controlled by delay coefficient generator 56 to pass one or more of the partially delayed receive waveforms to a beamform summer (not shown). The input to the delay line is shown as receive waveform $R_2$, and the output from the tap selector is shown as a delayed receive waveform $R_2'$.

It should be apparent that the delay systems shown in FIGS. 2 through 5 are merely four examples of a delay system that can apply time delays from associated delay profiles to respective channels of either a transmitter (FIGS. 2 and 3) or a receiver (FIGS. 4 and 5). These four embodiments should be taken merely as examples of a few of the many delay systems that can be used to implement the present invention.

More generally, the widest variety of hardware can be used to implement the ultrasound imaging system of FIG. 1. For example, any suitable transducer can be used, including 1, 1.5, and 2-dimensional transducers using either flat or curved arrays. Both digital and analog imaging systems can readily be adapted to implement the composite delay profiles described below.

Figure 6A:
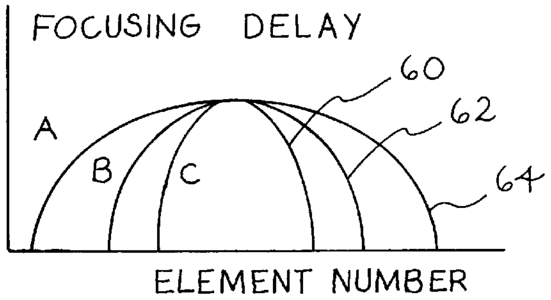
FIGS. 6*a*, 6*b* and 6*c* are diagrams illustrating a first preferred embodiment of the composite delay profile of this invention.
Figure 6C:
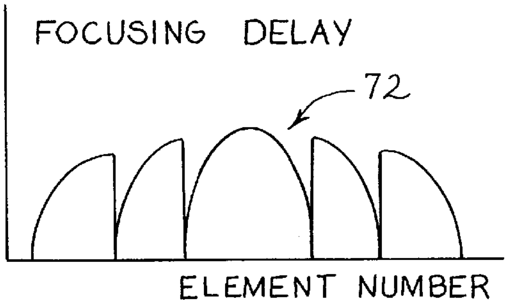
Figure 6B:
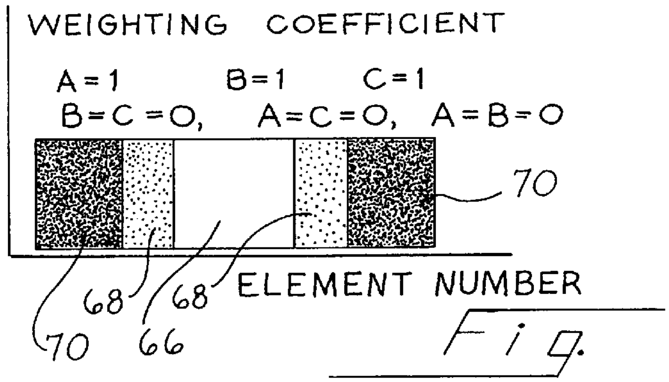

FIGS. 6*a* through 6*c* relate to a first composite delay profile that illustrates select features of this invention. FIGS. 6*a* and 6*b* are delay profile graphs in which the transducer element number is plotted on the horizontal axis and the time delays associated with the transducer elements are plotted on the Y axis. For example, a transducer element having 128 elements would have 128 separate time delays included in the delay profile.

FIG. 6*a* shows three separate point-focus delay profiles 60, 62, 64. Each of these point-focus delay profiles includes a set of time delays that cause ultrasonic transmit or receive signals to focus at a desired point For example, at a given range R=ct/2, the time delays needed to form a beam in direction θ focused to range R is in the Fresnel approximation:

$$\tau(x) = \frac{-x\sin\theta}{c} + \frac{x^2}{2Rc}\cos^2\theta \qquad \text{(Eq. 1)}$$

$$\tau(X) = \frac{-x\sin\theta}{c} + \frac{x^2}{c^2 t}\cos^2\theta = -\left(\frac{x}{c}\right)\sin\theta + \left(\frac{x\cos\theta}{c}\right)^2 \frac{1}{t} \qquad \text{(Eq. 2)}$$

An exact solution to the problem can be derived from geometrical considerations. Consider the case of a transducer array with a center transducer element $E_c$ and additional transducer elements $E_i$, where the desired focal point is situated at a distance $d_c$ from the center element $E_c$ along a line extending through the center element $E_c$ and perpendicular to the array. In this example, the elements $E_c$ and $E_i$ are separated by a distance w, and element $E_i$ is separated from the desired focal point by the distance $d_i$. The propagation path difference between the elements $E_i$ and $E_c$ is $$\Delta d = \sqrt{W^2 + d_c^2} - d_c \qquad \text{(Eq. 3)}$$

The time delay difference $\Delta t_i$ between the elements $E_c$, $E_i$ required to achieve the desired focus is $$\Delta t_i = \frac{1}{c}\left[\sqrt{w^2 + d_c^2} - d_c\right] \quad \text{(Eq. 4)}$$

As used herein, the term "point-focus delay profile" is intended to refer to a delay profile that causes ultrasonic waveforms to coherently add in (on transmit) or from (on receive) a relatively small physical region. This focusing region would of course have a physical extent, and is not in practice limited to a point. The point-focus delay profiles 60, 62, 64 are focused at separate respective ranges, with the delay profile 60 focused at a short range, the delay profile 62 focused at an intermediate range, and the delay profile 64 focused at a relatively long range.

FIG. 6*b* provides a graph of weighting coefficients for the respective transducer elements. In the graph of FIG. 6*b* the reference symbol 66 is used for a first set of transducer elements, the reference symbol 68 is used for a second set of transducer elements, and the reference symbol 70 is used for a third set of transducer elements.

FIG. 6*c* shows a composite delay profile 72 that has been generated from the point-focus delay profiles 60, 62, 64 of FIG. 6*a*, using the weighting coefficients of FIG. 6*b*. As shown in FIG. 6*c*, the composite delay profile 72 corresponds to the point-focus delay profile 60 for the first set of transducer elements 66, to the second point-focus delay profile 62 for the second set of transducer elements 68, and to the third point-focus delay profile 64 for the third set of transducer elements 70. In this example, three transmit or receive foci have been selected and the point-focus delay profiles 60, 62, 64 for these three foci have been used for the composite delay profile 72. The central part of the transducer aperture corresponding to the first set 66 of transducer elements is delayed by the point-focus delay profile 60 associated with the shortest range focus. Transducer elements in the next larger aperture (corresponding to the second set 68) are associated with the point-focus delay profile 62 for the next deeper transmit focus, and so forth.

It is preferable to select the point-focus delay profiles such that the time difference between two adjacent point-focus delay profiles at the points of transition is in each case equal to an integer multiple of the time of one period if the transmitted wave ($\lambda$/c).

Note that in the example of FIG. 6*a* through 6*c*, weighting coefficients have been limited to one and zero. In this example the transition between different point-focus delay profiles follows the aperture size or f-number, and the composite delay profile 72 is a combination of three point-focus delay profiles 60, 62, 64. In this way three separate transmit foci are provided within a single transmit event by applying different point-focus delay profiles to different sets of transducer elements. If desired, the transition from one point-focus delay profile to the next across the transducer aperture can be made at integer multiples of the ultrasonic wavelength.

Figure 7A:
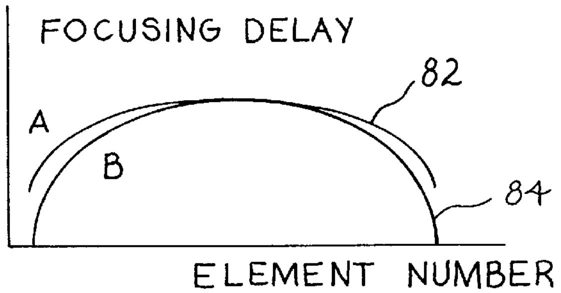
FIGS. 7*a*, 7*b* and 7*c* are diagrams illustrating a second preferred embodiment of the composite delay profile of this invention.
Figure 7C:
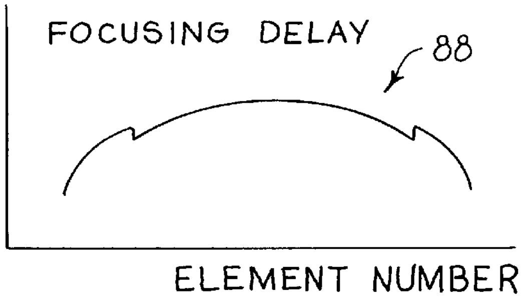
Figure 7B:
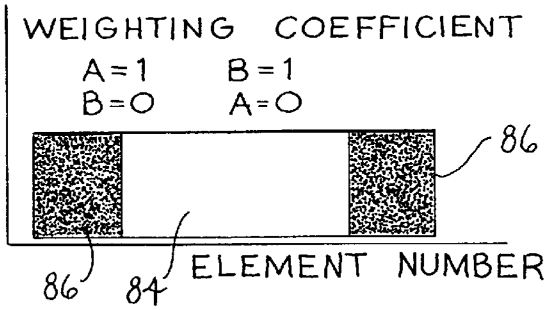

Another example of the composite delay profile of this invention is provided in FIGS. 7*a* through 7*c*. In this example the entire transducer aperture is divided into two or more equal or unequal segments. Each segment is then allocated a different point-focus delay profile. The preferred approach is to allocate the central region of the aperture to the more shallow focus and the periphery of the aperture to a deeper focus. In FIG. 7*a*two separate point-focus delay profiles 80, 82 focused at two different focal zones are shown. FIG. 7*b* shows the weighting coefficients used for the first set 84 of central transducer elements and the second set 86 of peripheral transducer elements. FIG. 7*c* shows the composite delay profile 88 that applies focusing delays appropriate for the shorter range focus to the central transducer elements and focusing delays appropriate for the longer range focus to the peripheral transducer elements.

Figure 8:
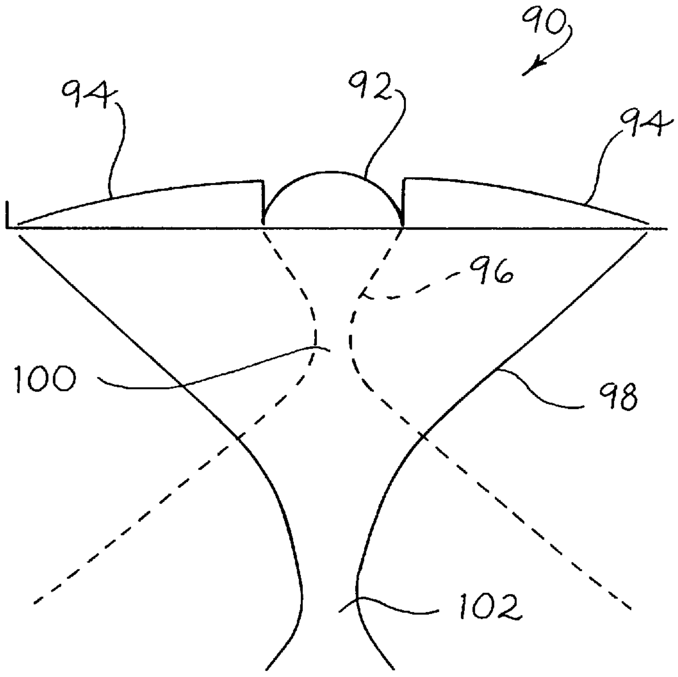
FIG. 8 is a diagram illustrating a third preferred embodiment of the composite delay profile of this invention.

FIG. 8 shows another composite delay profile 90 that in this case is composed of a first point-focus delay profile 92 associated with central transducer elements and a second point-focus delay profile 94 associated with peripheral transducer elements. The point-focus delay profile 92 is associated with a first beam profile 98 having a first focal zone 100, and the second delay profile 94 is associated with a second beam profile 98 having a second focal zone 102. Note that the second focal zone 102 is disposed at a deeper range than the first focal zone 100.

The composite delay profile 90 provides a shallow focus, and it extends the depth field as compared to a single focus. The transducer elements near the center of the array are focused in the shallow first focal zone 100 to improve near field performance. The second focal zone 102 improves far field performance.

Figure 9A:
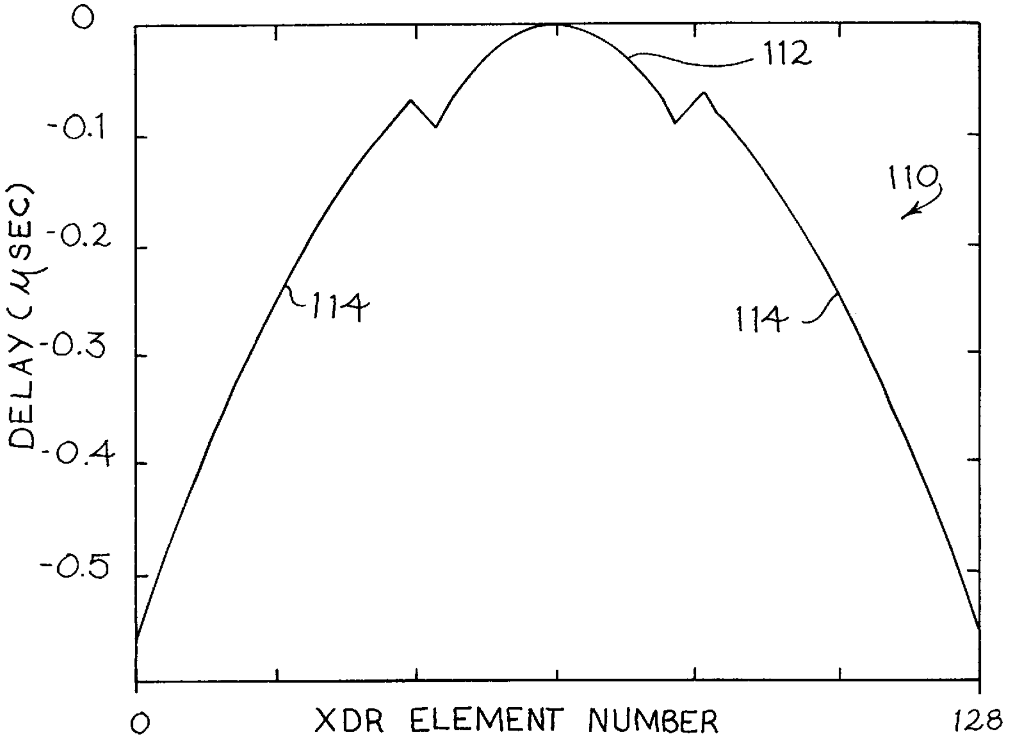
FIGS. 9*a* and 9*b* are schematic diagrams related to a fourth preferred embodiment of the composite delay profile of this invention.
Figure 9B:
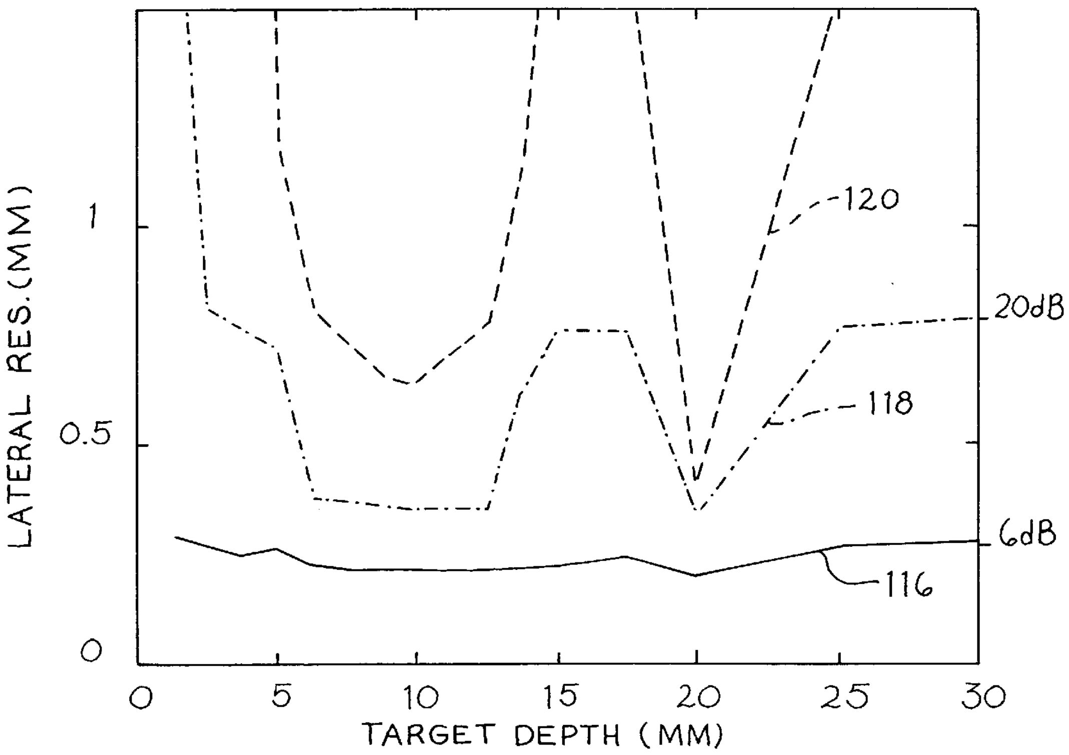

FIGS. 9*a* and 9*b* relate to a composite delay profile 110 that is composed of a first point-focus delay profile 112 and a second point-focus delay profile 114 for respective sets of transducer elements. As shown in FIG. 9*b*, the resulting composite beam profile is well formed, and provides −6 dB, −20 dB, and −30 dB beam profiles 116, 118, 120 as shown. In this case, the composite focusing provided by the composite delay profile 110 provides focus at both 10 and 20 millimeters.

Figure 10:
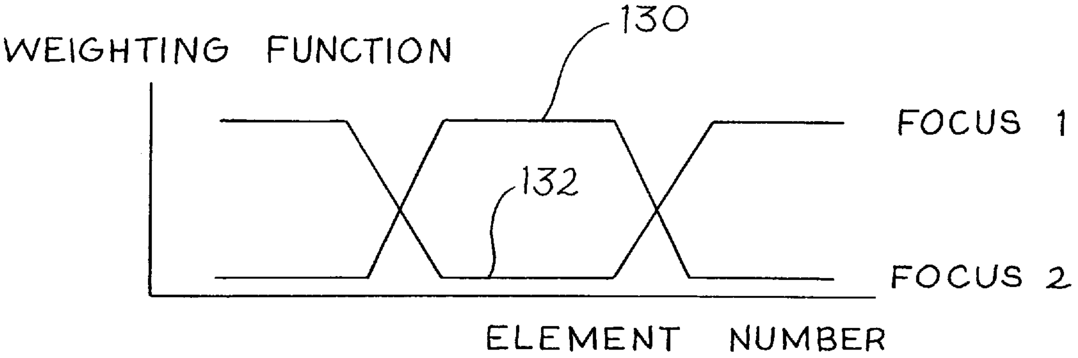
FIG. 10 is a diagram of a weighting function.

The foregoing examples have used two-level weighting factors to control transition from one point-focus delay profile to the next. Another approach suitable for use with this invention is to provide more gradual transitions between adjacent point-focus delay profiles in the composite delay profile. One possible weighting scheme for a dual-focus composite delay profile is shown in FIG. 10, in which weighting functions 130, 132 are provided for respective first and second point-focus delay profiles.

Figure 11A:
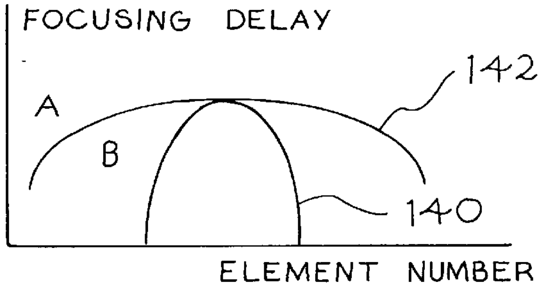
FIGS. 11*a*, 11*b* and 11*c* are schematic diagrams illustrating a fifth embodiment of the composite delay profile of this invention.
Figure 11C:
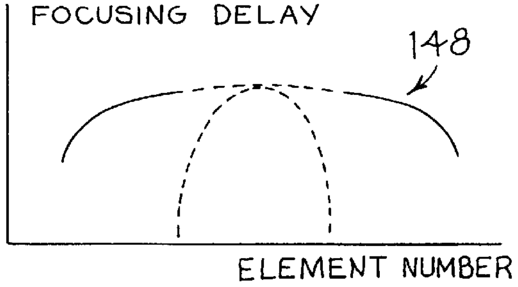
Figure 11B:
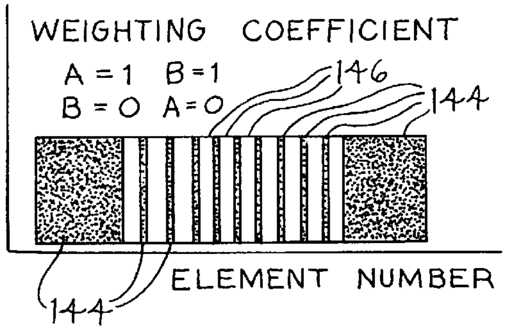

The foregoing examples have used sets of transducer elements that are contiguous for at least the central set associated with the central point-focus delay profile. Another alternative is to use alternating transducer elements for different ones of the available point-focus delay profiles. An example of this approach is shown in FIGS. 11*a* through 11*c*. In 11*a* two point-focus delay profiles 140, 142 are shown. The associated weighting coefficients are shown in FIG. 11*b*, in which the reference symbol 144 indicates transducer elements of the first set and the reference symbol 146 indicates the transducer elements of the second set. Note that the transducer elements in the first and second sets alternate in the central portion of the transducer aperture. The resulting composite delay profile 148 of FIG. 11*c* alternates between the two point-focus delay profiles in the central portion of the transducer aperture.

Figure 12:
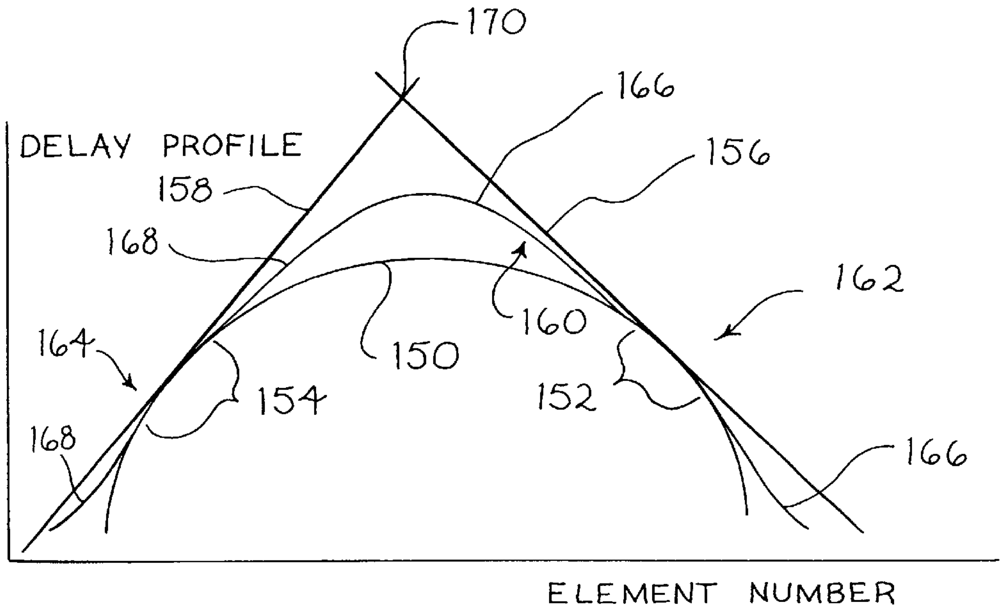
FIG. 12 is diagram illustrating a sixth embodiment of the composite delay profile of this invention.

FIG. 12 illustrates another composite delay profile 160. Again, transducer element number is plotted on the horizontal axis and time delay for the associated transducer element is plotted on the vertical axis. The composite delay profile 160 is related to a point-focus delay profile 150 that includes first and second parts 152, 154 on respective sides of the center of the transducer array. Two tangents 156, 158 have been drawn in FIG. 12, each tangentially oriented with respect to the point-focus delay profile 150 at a respective one of the first and second parts 152, 154. These two tangents 156, 158 intersect at an intersection 170. The composite delay profile 160 in this embodiment is a continuous function which may be considered for purposes of discussion as made up of four portions 162,164, 166, 168. The first and second portions 162, 164 that follow the point-focus delay profile 150 in the first and second parts 152, 154, respectively. The composite delay profile 160 also includes a third portion 166 positioned between the point-focus delay profile 150 and the tangent 156, and a fourth portion 168 positioned between the point-focus delay profile 150 and the tangent 158. The third and fourth portions 166, 168 meet between the intersection 170 of the first and second tangents 156, 158 and the point-focus delay profile 150. As shown in FIG. 12, the third portion 166 extends on both sides of the first portion 162 and the fourth portion 168 extends on both sides of the second portion 164.

Figure 13A:
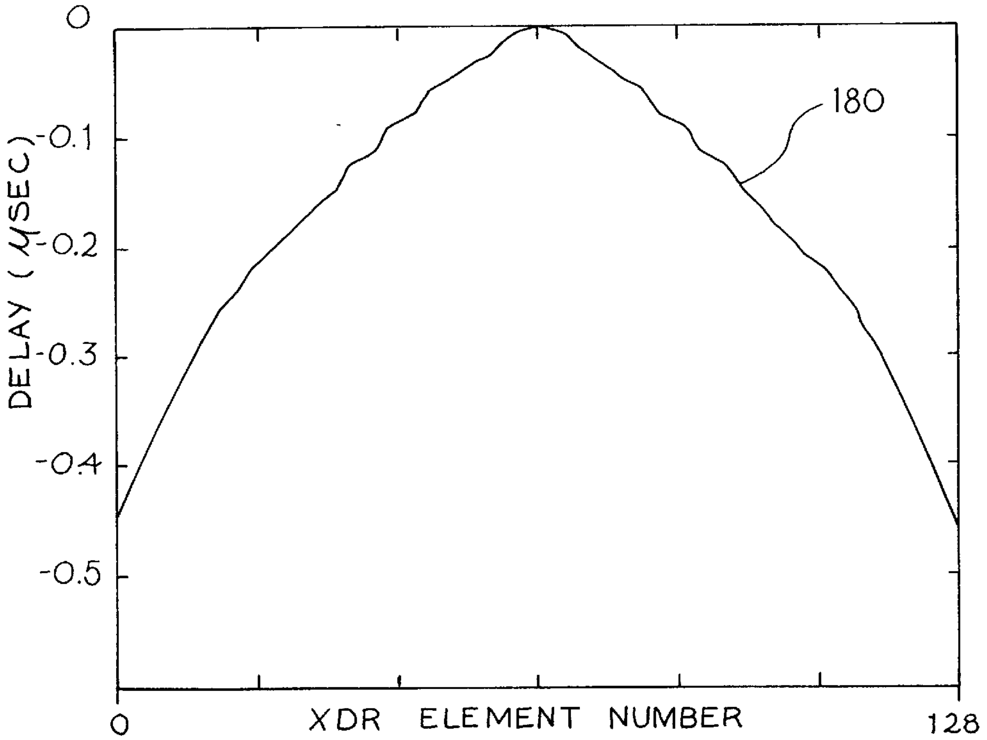
FIGS. 13*a*, 13*b* are diagrams related to a seventh embodiment of the composite delay profile of this invention.
Figure 13B:
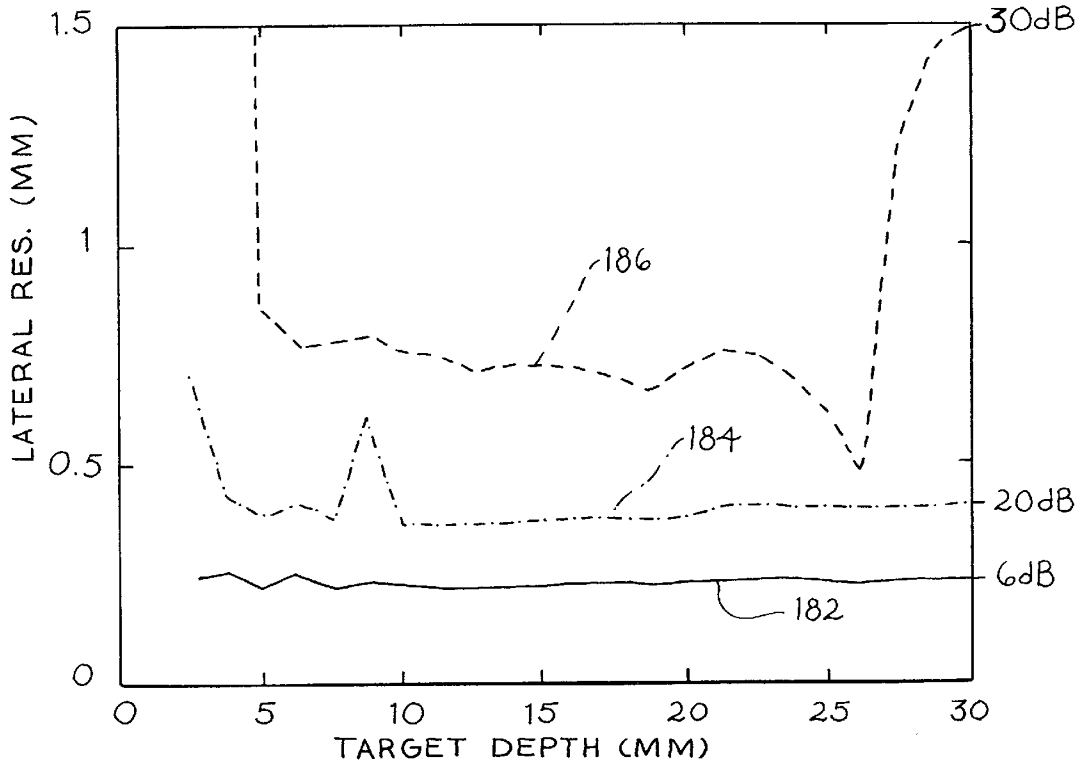

FIGS. 13*a* and 13*b* are related to a practical example of a composite delay profile 180 that is generated in a manner similar to that described above in conjunction with the composite delay profile 160 of FIG. 12. FIG. 13*a* shows the composite delay profile 180, and FIG. 13*b* shows the corresponding beam profiles as a function of target depth or range. In FIG. 13*b* the beam profiles at the −6 dB, −20 dB, and −30 dB signal levels are plotted using lines 182, 184, 186, respectively. As shown in FIG. 13*b*, the composite delay profile 180 results in a substantial extension in the depth of field.

Of course, it should be understood that many changes and modifications can be made to the preferred embodiments described above. For example, any of the composite delay profiles described above can be used in combination with multi-focus techniques, in which multiple delay profiles are superimposed for individual transducer elements. In this case the delay profile for one or more of the multi-focus delays is formed as described above, and the depth of field can be increased by a very large amount.

It should be apparent from the foregoing that novel techniques have been described for designing transmit or receive delay profiles to extend the depth of field. These techniques can be used for a wide variety of ultrasonic imaging modes, including fundamental imaging, contrast agent imaging, tissue harmonic imaging, B-mode imaging, Doppler imaging, M mode imaging, and so forth. In some applications it may be advantageous to use a transducer with a large aperture. In the examples described above the entire transducer aperture is utilized for each firing, and a large aperture with a large number of transducer elements may be particularly useful with this invention.

In the foregoing examples, the composite delay profiles have used multiple foci arranged along the same beam direction. In alternative embodiments the multiple foci of a single composite delay profile may be oriented along beams at different angles. An alternative way to design the composite delay profiles is to use an adaptive optimization routine to find the optimum focus delay based on beam width criteria.

As used herein the term “set” is intended broadly to encompass two or more. The term “coupled with” is intended broadly to encompass elements that are coupled together either directly or indirectly. Thus, first and second elements are said to be coupled with one another whether or not they are separated by intervening elements.

The foregoing detailed description has discussed only a few of the many forms that this invention can take. For this reason this detailed description is intended only by way of illustration. It is only the following claims, including all equivalents, that are intended to define the scope of this invention.

What is claimed is:

1. In a medical ultrasound imaging system comprising a transducer comprising an array of transducer elements, a transmitter coupled with the transducer, and a receiver coupled to the transducer and to a display processor, the improvement comprising:

at least one delay system coupled with the transducer, said delay system operative to form a delay profile for a plurality of the transducer elements within a single transmit event;

said delay profile comprising at least a first, substantially point-focus delay profile selectively applied to a first set of the transducer elements and not to a second set of the transducer elements during the single transmit event, and a second, substantially point-focus delay profile selectively applied to the second set of the transducer elements and not to the first set of the transducer elements during the single transmit event, said first and second delay profiles causing ultrasonic energy from the respective first and second sets of the transducer elements to constructively add at first and second respective spaced focal zones.

2. The invention of claim 1 wherein the delay profile additionally comprises a transitional delay profile for a third set of transducer elements intermediate the first and second sets of transducer elements.

3. The invention of claim 1 wherein the transducer elements of the first set are contiguous with one another.

4. The invention of claim 1 wherein at least some of the transducer elements of the first set are interleaved with at least some of the transducer elements of the second set.

5. The invention of claim 1 wherein the first focal zone is at a shorter range than the second focal zone and wherein the first set of the transducer elements is disposed more centrally than the second set of the transducer elements in the transducer.

6. The invention of claim 1 wherein the first and second delay profiles differ by about n $\lambda/c$ at a transition between the delay profiles, where n is a positive integer, $\lambda$ is a wavelength characterizing an ultrasonic pulse for the transducer, and c is the speed of sound.

7. The invention of claim 1 wherein the first and second spaced focal zones are spaced in range.

8. The invention of claim 1 wherein the first and second spaced focal zones are spaced in azimuth.

9. A medical ultrasound diagnostic imaging system comprising a transducer comprising an array of transducer elements, a transmitter coupled with the transducer, and a receiver coupled to the transducer and to a display processor, the improvement comprising:

at least one delay system coupled with the transducer, said delay system operative to form a delay profile characterized by a respective time delay for each of a respective plurality of the transducer elements within a single transmit event;

said delay profile comprising first and second portions that substantially correspond to respective parts of a point-focus delay profile, a third portion intermediate the point-focus delay profile and a first tangent to the point-focus delay profile at the first portion, and a fourth portion intermediate the point-focus delay profile and a second tangent to the point-focus delay profile at the second portion.

10. The invention of claim 9 wherein the third portion extends on both sides of the first portion.

11. The invention of claim 9 wherein the fourth portion extends on both sides of the second portion.

12. The invention of claim 9, 10 or 11 wherein the third and forth portions meet between an intersection of the first and second tangents and the point-focus delay profile.

13. The invention of claim 1 or 9 wherein the transmitter comprises at least one waveform generator operative to generate at least one transmit waveform, and wherein the delay system is operative to delay the at least one transmit waveform prior to application to the transducer elements.

14. The invention of claim 1 or 9 wherein the transducer elements generate respective receive waveforms, and wherein the delay system is responsive to a plurality of receive waveforms.

15. A medical ultrasound diagnostic imaging method for providing a delay profile for at least one ultrasonic waveform, said method comprising:

(a) delaying the at least one ultrasonic waveform during a first transmit event with a first, substantially point-focus delay profile applied to a first set of transducer elements included in a transducer but not to a second set of transducer elements included in the transducer;

(b) delaying the at least one ultrasonic waveform during said first transmit event with a second, substantially point-focus delay profile applied to the second set of transducer elements but not to the first set of transducer elements;

said first and second delay profiles causing ultrasonic energy associated with the ultrasonic waveforms for the respective first and second sets of transducer elements to constructively add at first and second respective spaced focal zones within said first transmit event.

16. The method of claim 15 further comprising (c) providing a transitional delay profile for a third set of transducer elements intermediate the first and second sets of transducer elements.

17. The method of claim 15 wherein the transducer elements of the first set are contiguous with one another.

18. The method of claim 15 wherein at least some of the transducer elements of the first set are interleaved with at least some of the transducer elements of the second set.

19. The method of claim 15 wherein the first focal zone is at a shorter range than the second focal zone, and wherein the first set of the transducer element is disposed more centrally than the second set of the transducer elements in the transducer.

20. The method of claim 15 wherein the first and second delay profiles differ by about n $\lambda/c$ at a transition between the delay profiles, where n is a positive integer, $\lambda$ is a wavelength characterizing the ultrasonic waveform, and c is the speed of sound.

21. The method of claim 15 wherein the first and second spaced focal zones are spaced in range.

22. The method of claim 15 wherein the first and second spaced focal zones are spaced in azimuth.

23. A medical ultrasound diagnostic imaging method for providing a delay profile for at least one ultrasonic waveform, said method comprising:

(a) delaying the at least one ultrasonic waveform during a first transmit event with first and second delay profile portions that substantially correspond to respective parts of a point-focus delay profile;

(b) delaying the at least one ultrasonic waveform during said first transmit event with a third delay profile portion intermediate the point-focus delay profile and a first tangent to the point-focus delay profile at the first portion;

(c) delaying the at least one ultrasonic waveform during said first transmit event with a third delay profile portion intermediate the point-focus delay profile and a second tangent to the point-focus delay profile at the second portion.

24. The method of claim 23 wherein the third portion extends on both sides of the first portion.

25. The method of claim 23 wherein the fourth portion extends on both sides of the second portion.

26. The method of claim 23, 24, or 25 wherein the third and forth portion meet between an intersection of the first and second tangents and the point-focus delay profile.

27. The method of claim 15 or 23 wherein the at least one ultrasonic waveform comprises at least one transmit waveform.

28. The method of claim 15 or 23 wherein the at least one ultrasonic waveform comprises at least one receive waveform.

* * * * *

UNITED STATES PATENT AND TRADEMARK OFFICE

CERTIFICATE OF CORRECTION

PATENT NO. : 6,312,386 B1 Page 1 of 1
DATED : November 6, 2001
INVENTOR(S) : Mirsaid Bolorforosh et al.

It is certified that error appears in the above-identified patent and that said Letters Patent is hereby corrected as shown below:

Column 2,
Line 43, delete "6b" and substitute -- 6a -- in its place.

Column 5,
Line 42, delete "period if" and substitute -- period of -- in its place.
Line 63, delete "7atwo" and substitute -- 7a two -- in its place.

Column 8,
Line 66, delete "forth" and substitute -- fourth -- in its place.

Signed and Sealed this

Fourteenth Day of January, 2003

JAMES E. ROGAN
*Director of the United States Patent and Trademark Office*